(12) United States Patent
Yang

(10) Patent No.: US 9,072,879 B2
(45) Date of Patent: *Jul. 7, 2015

(54) METHODS AND SYSTEM FOR ULTRASOUND-MEDIATED DRUG DELIVERY

(71) Applicant: NATIONAL YANG MING UNIVERSITY, Taipei (TW)

(72) Inventor: Feng-Yi Yang, Taipei (TW)

(73) Assignee: NATIONAL YANG MING UNIVERSITY, Taipei (TW)

( * ) Notice: Subject to any disclaimer, the term of this patent is extended or adjusted under 35 U.S.C. 154(b) by 183 days.

This patent is subject to a terminal disclaimer.

(21) Appl. No.: 13/728,753

(22) Filed: Dec. 27, 2012

(65) Prior Publication Data

US 2013/0261442 A1 Oct. 3, 2013

Related U.S. Application Data

(60) Provisional application No. 61/617,566, filed on Mar. 29, 2012.

(51) Int. Cl.
*A61M 37/00* (2006.01)
*A61B 8/08* (2006.01)
*A61K 9/00* (2006.01)

(52) U.S. Cl.
CPC ............ *A61M 37/0092* (2013.01); *A61B 8/481* (2013.01); *A61K 9/0009* (2013.01)

(58) Field of Classification Search
CPC .. A61B 8/481; A61K 9/0009; A61M 37/0092
USPC .......................................... 600/431; 601/2, 3
See application file for complete search history.

(56) References Cited

U.S. PATENT DOCUMENTS

| 7,896,821 B1 * | 3/2011 | Magnin et al. ..................... 601/2 |
| 2009/0074663 A1 * | 3/2009 | Lee et al. ..................... 424/1.69 |
| 2013/0261442 A1 * | 10/2013 | Yang ............................ 600/431 |

OTHER PUBLICATIONS

F. Yang et al., "Focused ultrasound and interleukin-4 receptor-targeted liposomal doxorubicin for enhanced targeted drug delivery and antitumor effect in glioblastoma multiforme," *Journal of Controlled Release*, 160 (2012), pp. 652-658.
F. Yang et al., "Treating gliobastoma multiforme with selective high-dose liposomal doxorubicin chemotherapy induced by repeated focused ultrasound," *International Journal of Nanomedicine*, 2012, 7: pp. 965-974.

* cited by examiner

*Primary Examiner* — Michael Rozanski
(74) *Attorney, Agent, or Firm* — Muncy, Geissler, Olds & Lowe, P.C.

(57) ABSTRACT

The present invention provides an ultrasound-mediated drug delivery method for administering a compound to a targeted tissue, and the method at least comprises the following steps: First, an ultrasound apparatus is provided. The compound is then administered to the targeted tissue. A sonication is performed by the ultrasound apparatus to a blood vessel of the targeted tissue after the administration of the compound, and the sonication is capable of enhancing the permeability of the blood vessel to allow the administration of the compound to the targeted tissue. An ultrasound-mediated drug delivery system is also disclosed here.

3 Claims, 15 Drawing Sheets

METHODS AND SYSTEM FOR ULTRASOUND-MEDIATED DRUG DELIVERY

CROSS-REFERENCE TO RELATED APPLICATIONS

This application claims benefit under 35 U.S.C 119(e) of U.S. Provisional Application No. 61/617,566, filed Mar. 29, 2012, the entire content of which is incorporated by reference herein.

FIELD OF THE INVENTION

The invention relates to a drug delivery system and method, especially relates to a novel ultrasound enhanced drug delivery system and method of delivering a compound using such system.

BACKGROUND OF THE INVENTION

In present medical technology, delivering the drug to a lesion zone without passing the metabolism of the digestive system and the liver to maintain the concentration of the drug in the blood is a concerned research subject. However, it is difficult to deliver the drug to the lesion zone directly.

For example, the direct delivery of drugs to the central nervous system would make the resulting interactions highly target-specific and thereby dramatically improve the therapeutic effects and reduce possible side effect. However, it is difficult to delivery many potent therapeutic agents to the brain due to the presence of the blood-brain barrier, which is a specialized system of capillary endothelial cells that protects the brain from harmful substances. Although many methods have been developed to overcome the blood-brain barrier impermeability when delivering drugs, such as increasing their liquid solubility, or by the using vectors such as amino acids for carriers, none has been applied clinically.

Furthermore, the concentration of chemotherapeutics required to achieve clinically effective cytotoxicity in tumors is limited by the associated tissue toxicity and by physiologic barriers that prevent the delivery of drug to the tumor. Liposome-based drug-delivery systems have been designed to elevate tumor drug levels while limiting systemic drug exposure. It is thought that targeted delivery of liposomes encapsulating cytotoxic drugs should increase the accumulation and retention of drugs at the tumor site. The employment of liposomal chemistry, such as liposomes conjugated to antibodies or targeting ligands, can optimize and enhance the local delivery and better drug cell internalization compared with the free drug.

The therapeutic effect of a drug can be effectively increased when tissue-specific delivery of the drug is coupled to targeted biomarkers that may be expressed in certain disease conditions. This may also result in enhanced drug deposition while limiting systemic drug exposure. However, because each disease condition displays a different subset of biomarkers, and because each individual persons' biomarkers associated with a certain disease may be expressed at varying levels, the effects of targeted drugs may vary and sometime are less effective than expected.

SUMMARY OF THE INVENTION

According to the abovementioned disadvantages of the prior art, the present invention provides an ultrasound-mediated drug delivery method for administering a compound to a targeted tissue, and the method at least comprises the following steps: First, an ultrasound apparatus is provided. The compound is then administered to the targeted tissue. A sonication is performed by the ultrasound apparatus to a blood vessel of the targeted tissue after the administration of the compound, and the sonication is capable of enhancing the permeability of the blood vessel to allow the administration of the compound to the targeted tissue.

Preferably, the method provided in the present invention further comprises the following a step of injecting an ultrasound contrast agent. Preferably, the ultrasound contrast agent comprises microbubbles.

Preferably, the method provided in the present invention further comprises the following steps after 1-10 days from the step of performing the sonication to the blood vessel of the targeted tissue by the ultrasound apparatus: First, the step of administering the compound to the targeted tissue is repeated. And then, an another sonication will be performed to the blood vessel of the targeted tissue by the ultrasound apparatus. Preferably, the compound is administered with a lower dose of 3-5 mg/kg.

Preferably, the method provided in the present invention further comprises the following steps after the step of performing the sonication to the blood vessel of the targeted tissue by the ultrasound apparatus: First, the targeted tissue is stayed for an appropriate period. Another one sonication is performed to the blood vessel of the targeted tissue. Preferably, the compound is administered with a higher dose of 10-15 mg/kg.

Preferably, the appropriate period depends on the half-life of the compound.

Preferably, the appropriate period has a value between 1 minute and 6 hours.

Preferably, the sonication and the another sonication are performed with a frequency of between about 20 kHz to 10 MHz.

Preferably, the sonication and the another sonication are performed for a period between about 10 seconds to 30 minutes.

Preferably, the compound is administered in the form of a liposome, a liquid, a powder, a particle, microbubbles, microspheres, nanospheres, nanoparticles and combinations thereof.

The present invention further provides an ultrasound-mediated drug delivery system for administering a compound to a targeted tissue. The system at least comprises an ultrasound apparatus and a compound. The compound is capable of being administered to the targeted tissue. A sonication is performed by the ultrasound apparatus to a blood vessel of the targeted tissue after the administration of the compound, and the sonication is capable of enhancing the permeability of the blood vessel to allow the administration of the compound to the targeted tissue.

Preferably, the ultrasound apparatus is a focused ultrasound apparatus. Preferably, the system comprises a function generator, an amplifier, a power meter and a transducer. The function generator for generating the sonication. The amplifier connected with the function generator to amplify the sonication. The power meter connected with the amplifier, and the transducer connected between the power meter and a removable cone for transferring the sonication to the blood vessel of the targeted tissue.

Preferably, the system provided in the present invention further comprises an ultrasound contrast agent injected before the administration of the compound, and the ultrasound agent comprises microbubbles.

Preferably, the compound is capable of being administered to the targeted tissue repeatedly after performing the sonication to the blood vessel of the targeted tissue, and the ultrasound apparatus further performs an another sonication to the blood vessel of the targeted tissue after the administration of the compound.

Preferably, the ultrasound apparatus performs another one sonication to the blood vessel of the targeted tissue after staying the targeted tissue for an appropriate period. Preferably, the appropriate period has a value between 1 minute and 6 hours.

Preferably, the sonication and the another sonication are performed with a frequency of between about 20 kHz to 10 MHz.

Preferably, the sonication and the another sonication are performed for a period between about 10 seconds to 30 minutes.

Preferably, the compound is a therapeutic agent or a diagnostic agent.

Preferably, the compound is an imaging agent.

Preferably, the compound is conjugated to a targeting moiety. Preferably, the targeting moiety is a transducing peptide, a natural receptor ligand, a phage-display selected peptide ligand, a fragment of an endogenous protein, an antibody or antibody fragment to a receptor, a small molecule, a nonendogenous protein or fragments thereof. Preferably, the targeting moiety is AP-1.

Preferably, the compound is administered in the form of a liposome, a liquid, a powder, a particle, microbubbles, microspheres, nanospheres, nanoparticles and combinations thereof.

Preferably, the targeted tissue is a tumor tissue. Preferably, the tumor tissue is a brain tumor tissue, ovarian tumor tissue, breast tumor tissue, liver tumor tissue, kidney tumor tissue, head and neck tumor tissue, colon tumor tissue, and combinations thereof.

Preferably, the targeted tissue is associated with tissue specific marker. Preferably, the tissue specific marker is associated with a disease condition. Preferably, the disease condition is cancer, infectious disease, immunological disease, cardiovascular disease, respiratory disease, neurological disease and combinations thereof.

Preferably, the compound is capable of treating or preventing cancer. Preferably, the cancer is brain cancer, ovarian cancer, breast cancer, liver cancer, kidney cancer, head and neck cancer, colon cancer and combinations thereof.

The features and advantages of the present invention will be understood and illustrated in the following specification and FIGS. 1-14B.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. And further, the following terms and phrases as used herein have the meanings ascribed to them unless specified otherwise:

As used herein the specification, "a" or "an" may mean one or more.

A "therapeutic agent" refers to and encompasses an atom, molecule, or compound that is useful in preventing and/or treating a disease.

A "diagnostic agent" refers to and encompasses an atom, molecule, or compound that is useful in diagnosing a disease. Diagnostic agents include, but are not limited to, radioisotopes, dyes, contrast agents, fluorescent compounds or molecules and enhancing agents (e.g., paramagnetic ions). A non-radioactive diagnostic agent is a contrast agent suitable for magnetic resonance imaging, computed tomography or ultrasound.

An "imaging agent" refers to and encompasses an atom, molecule or compound that is useful in detecting physical changes or produces images of internal body tissues. In some aspects, the imaging agent may be a diagnostic agent.

The term "treatment" and "treat", and the like, refers to and encompasses therapeutic or suppressive measures for a disease or disorder leading to any clinically desirable or beneficial effect, including, but not limited to, alleviation or relief of one or more symptoms, regression, slowing or cessation of progression of the disease or disorder. Treatment can be evidenced as a decrease in the severity of a symptom, the number of symptoms, or frequency of relapse.

The terms "preventing," "inhibiting," "reducing" or any variation of these terms, includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99% or more, or any range derivable therein, reduction of activity or symptoms, compared to normal.

A "subject" shall refer to and encompass a human or other animal. For example, the animal may be a primate or a non primate and may include without limitation a rabbit, bovine, equine, pig, rat, mouse, dog or cat.

For clarity of disclosure, and not by way of limitation, the detailed description of the invention is divided into the subsections which follow.

Figure 1:
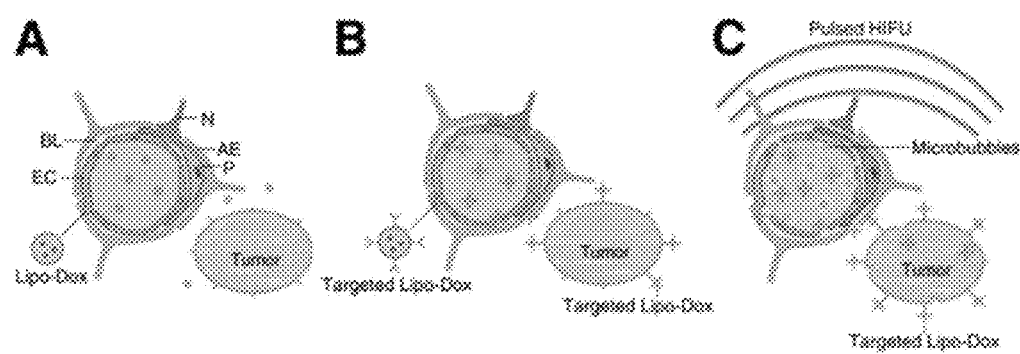
FIG. 1 is a diagram showing a schematic depiction of the synergistic treatment strategy.
Figure 2:
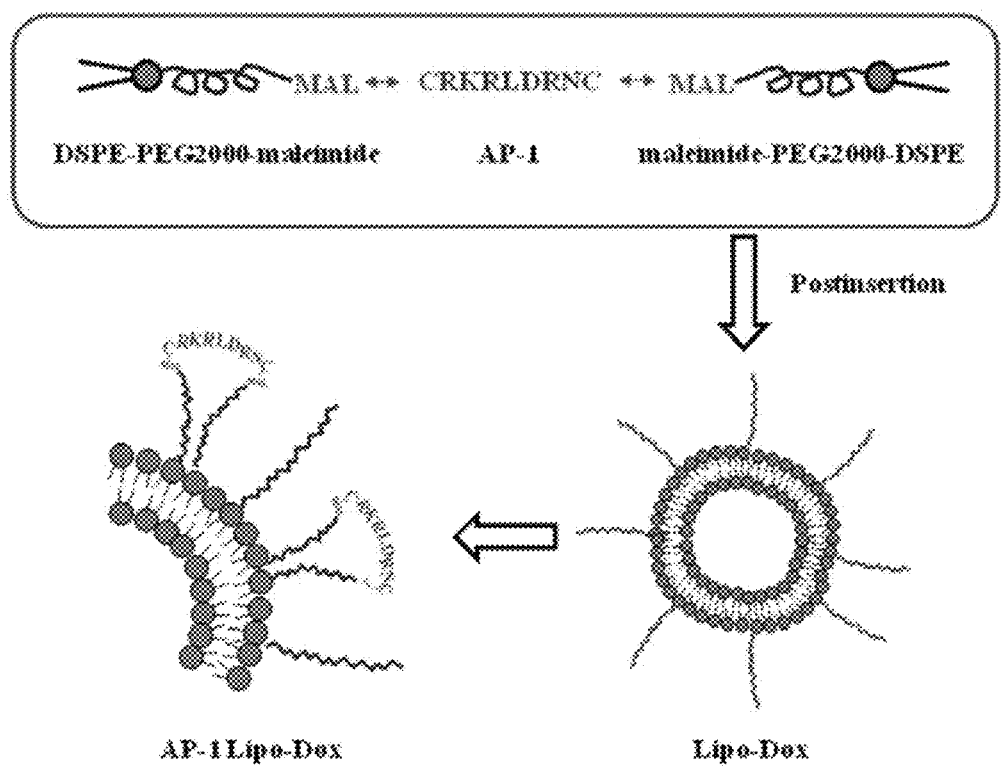
FIG. 2 is a diagram showing two different compounds used in the present invention.

According to the abovementioned situation and previous studies, it has shown that poor penetration and limited distribution of doxorubin (Dox) in solid tumors are the main causes of its inadequacy as a chemotherapeutic agent. Therefore, please refer to FIG. 1 and FIG. 2, FIG. 1 is a diagram showing a schematic depiction of the synergistic treatment strategy and FIG. 2 is a diagram showing two compounds used in the present invention. As shown in FIG. 1, a novel peptide the Applicant designed as a ligand from atherosclerotic plaque-specific peptide-1 (hereafter "AP-1") was selected from phage display libraries that can locate atherosclerotic plaque tissue and bind to the IL-4 receptor, since it has the same binding motif to the IL-4 protein. AP-1-labeled nanoparticles were used for the targeted drug delivery to tumor. And then, pulsed HIFU exposures were combined with AP-1-conjugated liposomes to enhance the targeted delivery of doxorubicin (Dox) into tumors. Furthermore, the present invention provides actively targeting nanoparticles by conjugating AP-1 to the surface of liposomes to provide a potential antitumor treatment for brain tumors as shown in FIG. 2.

Figure 3:
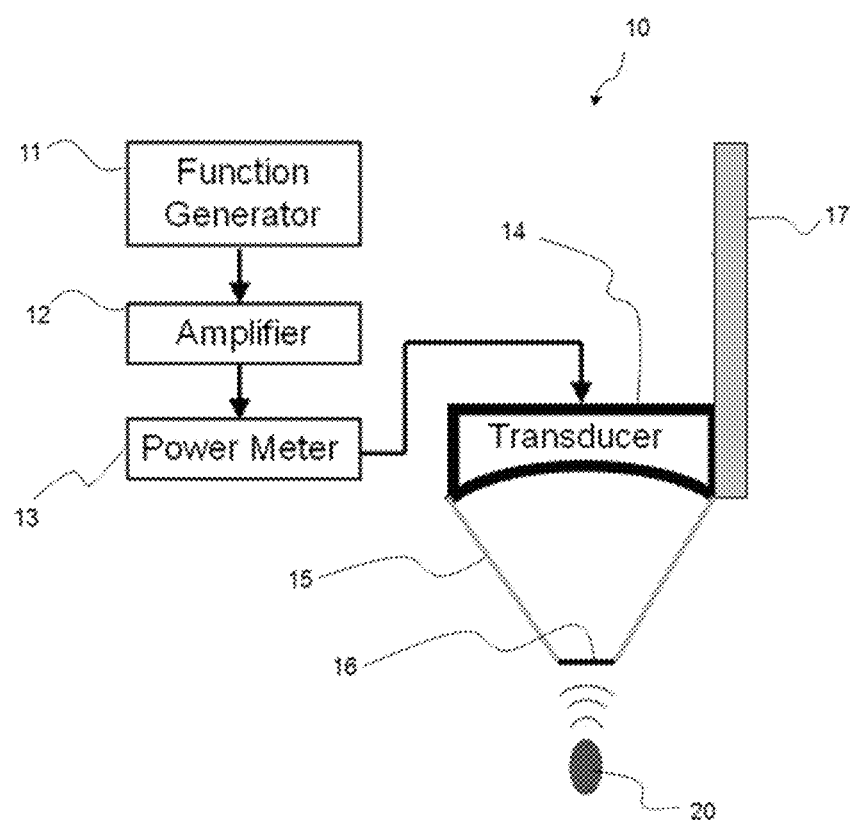
FIG. 3 is a diagram showing the frame of an ultrasound-mediated drug delivery system according to an preferred embodiment of the present invention.

In the following, an ultrasound-mediated drug delivery system and a method using such system will be described as FIG. 3 and FIG. 4. Please refer to FIG. 3 first, FIG. 3 is a diagram showing the frame of an ultrasound-mediated drug delivery system according to an preferred embodiment of the present invention. As shown in the figure, an ultrasound-mediated drug delivery system is disclosed in the present invention and at least comprises an ultrasound apparatus 10 and a compound (not shown in the figure).

Preferably, the ultrasound apparatus 10 is a focused ultrasound apparatus for focusing its ultrasound energy on a specific zone and comprises a function generator 11, an amplifier 12, a power meter 13 and a transducer 14. The transducer 14 is mounted on a removable cone 15 filled with degassed water whose tips is sealed with a polyurethane membrane 16, and the center of the focal spot is positioned approximately distance below the tip of the cone 15, however, the invention is not limited thereto. And then, the transducer 14 is attached to a stereotaxic apparatus 17 that allowed 3-D positioning.

As shown in FIG. 3, the function generator 11 is connected to the power amplifier 12 to amplify a sonication generated by the function generator 11, and the sonication is then delivered to the transducer 14 via an electrical matching network. Finally, the ultrasound apparatus 10 performs the sonication to a blood vessel (not shown in the figure) of the targeted tissue 20 to allow the compound passing through the blood vessel into the targeted tissue 20.

Preferably, the sonication is performed in a continuous manner, pulse manner, modulated manner and combinations thereof. Preferably, the ultrasound apparatus 10 will not have only one transducer and more than one ultrasound transducer may be used. For example, at least two, three, four or more ultrasound transducers may be used. In other embodiments, the ultrasound transducer may be a single-element transducer. In other embodiments, the ultrasound transducer may be a multiple-element transducer. In other embodiments, the ultrasound transducer may be a phase-arrayed transducer. In still other embodiments, the ultrasound transducer may be helmet type transducer. However, the present invention is not limited thereto.

Although the figure does not show an ultrasound contrast agent, however, the system provided in the present invention further comprises the above ultrasound contrast agent. Preferably, the ultrasound contrast agent comprises microbubbles, and it needs to be noted that those microbubbles initially from. And then the microbubbles grow in successive cycles and subsequently reach to unstable size. Finally, the microbubbles undergo violent collapse. The former part is stable cavitation. The latter part is inertial cavitation. By this means, many physical effects can be produced, including radiation force, bubble oscillation, and acoustic streaming. It means those microbubbles increase the permeability of the blood vessel of the targeted tissue. Moreover, the microbubbles are not limited to combine with the compound. That is, the microbubbles can be injected to the targeted tissue before the administration of the compound, or the compound can be administered in a form of the microbubbles. The present invention is not limited thereto.

In a preferred embodiment of the present invention, the abovementioned ultrasound apparatus 10 exposures were generated by a 1.0-MHz, single element focused transducer (A392S, Panametrics, Waltham, Mass., USA) with a diameter of 38 mm and a radius of curvature of 63.5 mm. The focal zone of the therapeutic transducer was in the shape of an elongated ellipsoid, with a radial diameter (−6 dB) of 3 mm and an axial length (−6 dB) of 26 mm. The ultrasound driving system and equipment setup were the same as used in our previous study. UCA (SonoVue, Bracco International, Amsterdam, The Netherlands) was injected into the tail vein of the mice about 10 s before each sonication. This agent contains phospholipid-coated microbubbles at a concentration of $1$-$5 \times 10^8$ bubbles/ml, with the bubbles having a mean diameter of 2.5 μm. The sonication was precisely targeted using a stereotaxic apparatus that utilized the bregma of the skull as an anatomical landmark. The ultrasound beam was delivered to one location in the left brain hemisphere, centered on the tumor injection site. The following sonication parameters were used: an acoustic power of 2.86 W (corresponding to a peak negative pressure of 0.7 MPa) with an injection of 300 μl/kg UCA, a pulse repetition frequency of 1 Hz, and a duty cycle of 5%. And further, a group of control mice was injected with GBM8401 glioma cells, but received no treatment. Five and 9 days after tumor cell implantation, the other glioma-bearing mice received one of the following: (1) pulsed-HIFU exposure, (2) AP-1 Lipo-Dox, or (3) AP-1 Lipo-Dox followed by pulsed HIFU. The concentration of liposomes administered to the mice via tail-vein injection corresponded to 5 mg/kg. The detail and the results of the above treatments will be illustrated later, and the present invention is not limited to the above chemical, dose and ratio.

The compound is capable of being administered to the targeted tissue 20. Preferably, the compound is a therapeutic agent or a diagnostic agent, and the therapeutic agent can be a chemotherapeutic agent, immunomodulatory agent or antibody. For example, such chemotherapeutic agents may include anthracyclines, such as doxorubicin and epirubicin; anthracene diones, such as mitoxantrone; and taxanes, such as paclitax or docetaxel. The chemotherapeutic agent, or a mixture or combination of such agents may be use in this invention. In some embodiments, the compound may be doxorubicin, paclitaxel, docetaxel and combinations thereof. The compounds may also include but are not limited to those for the palliative, prevention or treatment of cancers, infectious diseases, immunological diseases, cardiovascular diseases, respiratory diseases, neurological diseases. Such compounds may include but are not limited to interleukins (i.e., IL-1, IL-2, IL-3, IL-4, IL-5, IL-6, IL-7, IL-8, IL-9 and IL-10), interferons, and tumor necrosis factor (i.e., TNF-α and TNF-β).

In some embodiments, the compound may be conjugated to a targeting moiety. The targeting moiety is selected based on the target cell type, tissue, or organ to allow sufficiently specific delivery of the compound to the desired target. Examples of targeting moieties may include but are not limited to transducing peptides, natural receptor ligands, phage-display selected peptide ligands, fragments of endogenous proteins, antibodies or antibody fragments to receptors, small molecules, non-endogenous proteins and fragments thereof.

In some embodiments, the targeting moiety may be is associated with tissue specific marker. The tissue specific marker may be associated with a disease condition. In some embodiments, the disease condition is cancer, infectious disease, immunological disease, cardiovascular disease, respiratory disease, neurological disease, and combinations thereof. In some embodiments, the targeting moiety comprises the atherosclerotic plaque-specific peptide-1 (AP-1). In some embodiments, AP-1 comprises the amino acid sequence CRKRLDRNC.

Preferably, the compound is administered in the form of a liposome, a liquid, a powder, a particle, microbubbles, microspheres, nanospheres, nanoparticles and combinations thereof, and to the targeted tissue before ultrasound energy delivery, during ultrasound energy delivery, after ultrasound energy delivery and combinations thereof. In some embodiments, the compound is administered in the form of a liposome. In some embodiments, the compound being delivered by a liposome is a chemotherapeutic agent such as doxorubicin. In some embodiments, a liposome delivering the compound is conjugated to a targeting moiety. For example, a liposome delivering a chemotherapeutic agent such as doxorubicin may be conjugated to a targeting moiety such as AP-1.

Preferably, the targeted tissue 20 is a tumor tissue and can be selected from a group consisting of a brain tumor tissue, ovarian tumor tissue, breast tumor tissue, liver tumor tissue, kidney tumor tissue, head and neck tumor tissue, colon tumor tissue and their combinations. Furthermore, the targeted tissue can be associated with tissue specific marker. Preferably, the tissue specific marker is associated with a disease condition, and the disease condition is cancer, infectious disease, immunological disease, cardiovascular disease, respiratory disease, neurological disease and combinations thereof.

Preferably, the compound is capable of treating or preventing cancer, infectious disease, immunological disease, cardiovascular disease, respiratory disease, neurological disease, and combinations thereof. Preferably, the cancer is brain cancer, ovarian cancer, breast cancer, liver cancer, kidney cancer, head and neck cancer, colon cancer and combinations thereof.

Figure 4:
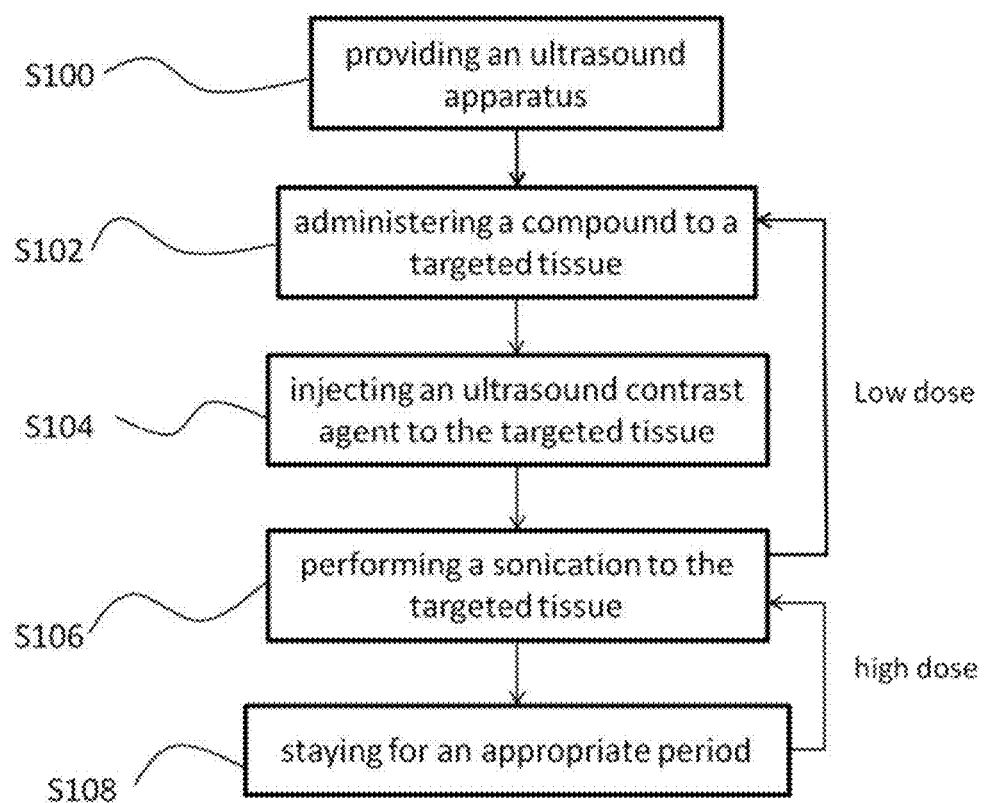
FIG. 4 is a flow chart showing an ultrasound-mediated drug delivery method according to the preferred embodiment of the present invention.

Please refer to FIG. 4, FIG. 4 is a flow chart showing an ultrasound-mediated drug delivery method according to the preferred embodiment of the present invention. As shown in the figure, an ultrasound-mediated drug delivery method using the abovementioned system is disclosed therein and comprises the following steps. In a first step S100, an ultrasound apparatus is provided. The compound is administered to the targeted tissue as shown in step S102, and an ultrasound contrast agent is injected to the targeted tissue in step S104. A sonication is performed in step S106 by the ultrasound apparatus to a blood vessel of the targeted tissue after the administration of the compound, and the sonication is capable of enhancing the permeability of the blood vessel to allow the administration of the compound to the targeted tissue. Preferably, the ultrasound contrast agent comprises microbubbles, and the compound is preferably administered with a dose of 5 mg/kg. It is noted that the abovementioned dose of 5 mg/kg is only an embodiment for representing a lower dose applied on the mice, and it is not suitable for applying on human or other animals. In the preferred embodiment, the above low dose is between 3 mg/kg and 5 mg/kg. On the other hand, the step S102 will be repeated while the used compound is administered with a lower dose, and an another sonication will be performed after the administration of the compound. That is, the steps S102 to S106 can be performed repeatedly according to the efficiency of the curing or the dose of the compound.

Furthermore, the abovementioned system and method are also applied for administering the compound with high dose to the targeted tissue. Please keep referring to FIG. 4. When the compound is administered with a higher dose, such as 10 mg/kg for the mice. In the preferred embodiment, the above high dose is between 10 mg/kg and 15 mg/kg. The method provided in the present invention further comprises the following steps after the step of performing the sonication to the blood vessel of the targeted tissue by the ultrasound apparatus. First, the targeted tissue is stayed for an appropriate period in step S108. Another one sonication is then performed to the blood vessel of the targeted tissue. That is, the steps S106-S108 will be repeated to increase the permeability of the blood vessel of the targeted tissue.

Preferably, the appropriate period depends on the half-life of the compound and has a value between 1 minute and 6 hours. Preferably, the sonication and the another sonication are performed with a frequency of between about 20 kHz to 10 MHz. Preferably, the sonication and the another sonication are performed for a period between about 10 seconds to 30 minutes. On the other hand, the repeated times of the steps S106-S108 are not limited and depend on the administering efficiency of the compound.

After illustrating the ultrasound-mediated drug delivery system and method as above, the related experimental sections will be described in the following to further illustrate each steps of the present invention.

First, the sonication parameters have been described as above so that there is no more explanation of using the ultrasound apparatus. And then, all procedures were performed according to the guidelines of and were approved by the Animal Care and Use Committee of the National Yang-Ming University. Male 6- to 8-week-old NOD-scid mice were anesthetized via an intraperitoneal administration of pentobarbital at a dose of 40 mg/kg body weight. Their heads were shaved above the nape of the neck, scrubbed with Betadine/alcohol, and immobilized in a Cunningham Mouse/Neonatal Rat Adaptor stereotactic apparatus (Stoelting, Wood Dale, Ill., USA). A 5-mm skin incision was made along the sagittal suture and a burr hole drilled into the skull. Then, $2\times10^5$ human brain malignant glioma cells (GBM8401) in 2 µl of culture medium were injected stereotactically into a single location in each left hemisphere (0.14 mm anterior and 2.0 mm lateral to the bregma) of each mouse at a depth of 3.5 mm from the brain surface. The burr holes in the skull were then sealed with bone wax and the wound was flushed with iodinated alcohol. Biophotonic imaging was used to determine that a tumor was established.

Second, Lipo-Dox was prepared using a solvent injection method plus remote loading procedures. Briefly, hydrogenated soybean L-α-phosphatidylcholine (95.8 mg), cholesterol (31.9 mg), and 1,2-distearoyl-sn-glycero-3-phosphoethanolamine-N-[methoxy(polyethylene glycol)-2000] (DSPEPEG2000, 31.9 mg, Avanti Polar Lipids) were dissolved and well mixed in 1 ml of absolute ethanol at 60° C. The lipid and ethanol mixture was then injected into a 9-ml solution of 250 mM ammonium sulfate and stirred for 1 h at 60° C. The mixture was then extruded five times through polycarbonate membranes (Isopore Membrane Filter, Millipore) with pore sizes of 0.4, 0.2, 0.1, and 0.05 µm, consecutively, at 60° C. with high-pressure extrusion equipment (Lipex Biomembranes) to produce small liposomes. The liposome suspension was then dialyzed five times against large amounts of 10% sucrose containing 5 mMNaCl to remove the unentrapped ammonium sulfate and ethanol. After dialysis, the liposome suspension was placed in a 50-ml glass bottle in a 60° C. water bath and mixed with Dox, to a final Dox concentration of 2 mg/ml in 10% sucrose solution. The bottle was intermittently shaken in a 60° C. water bath for 1 h and then immediately cooled down to 4° C., culminating in the production of Lipo-Dox.

Due to the presence of a thiol group on each cysteine of the AP-1 peptide, it is possible to couple AP-1 to liposomes via the thiol-maleimide reaction. Briefly, AP-1 peptide was conjugated to 1,2-distearoyl-sn-glycero-3-phosphoethanolamine-N-[maleimide(polyethylene glycol)-2000] by adding AP-1 to the DSPE-PEG2000-MAL micelle solution at a 2:1 molar ratio while mixing at 4° C. overnight. The free thiol groups were measured with 5,5'-dithiobis-(2-nitrobenzoic acid) at 420 nm to confirm that most of the AP-1 was conjugated with DSPE-PEG2000-MAL after the reaction. AP-1-conjugated DSPE-PEG2000 was transferred into the preformed Lipo-Dox at a 1.5% molar ratio of total lipid components and incubated at 60° C. for 1 h to obtain AP-1-labeled Lipo-Dox as shown in FIG. 2.

The resulting unconjugated Lipo-Dox and AP-1 Lipo-Dox were found to have particle diameters of 100-120 nm, as measured by a dynamic light-scattering apparatus (Coulter N4 plus, Beckman), as well as a surface zeta potential of between −20 and −30 mV, as measured by electrophoretic light scattering (ZetaPlus, Brookhaven).

After preparing all the compounds and performing the sonication, several analytical tests are then performed to check the therapeutic efficiency. A quantitative analysis of Dox is performed first. An overdose of pentobarbital was used to put animals into a state of deep anesthesia. The brain was perfused by transcardiac methods with normal saline 3.5 h after the Dox administration in order to flush unabsorbed Dox from the cerebral vessels. The site of tumor tissue was harvested along with its contralateral counterpart as a control. Dox was extracted from the tumor and control tissues by homogenization and refrigeration for 24 h in 20 volumes of acidified ethanol at 4° C. Tissues were centrifuged at 16,000×g for 25 min at 4° C. and the supernatant was stored at −20° C. until being used in a fluorometric assay. The concentration of Dox present was measured using a spectrophotometer (PowerWave 340, BioTek, USA; excitation at 480 nm and emissions measured at 590 nm), with the value determined by taking the average of at least three fluorometric readings. The Dox present in the tissue samples was quantified using a linear regression standard curve derived from seven different concentrations of Dox; the amount of Dox was quantified as the absorbance per gram of tissue.

And then, a biophotonic tumor imaging is proceeded as the following. Tumor size was quantified by analyzing biophotonic images obtained from 5 to 16 days after tumor implantation. The GBM8401 cell lines were transformed with the luciferase gene, and each mouse was injected with 4.29 mg of freshly prepared luciferin substrate suspended in phosphate-buffered saline (PBS). After anesthetic induction with isoflurane (1.5 l/min oxygen in 4% isoflurane), mice were imaged using the Xenogen IVIS imaging system (Xenogen, Palo Alto, Calif., USA) 10 min after the intraperitoneal injection of luciferin, with a 1-min acquisition time in small-bin mode. Luciferase activity was viewed and quantified using Living Image Software from Xenogen within a region of interest that encompassed the head of the mouse after administration of luciferin substrate to the anesthetized mouse.

Third, Magnetic resonance imaging (MRI) was performed using a 3-T MRI system (TRIO 3-T MRI, Siemens MAGNETOM, Germany) after focused ultrasound sonication. The mice were anesthetized with isoflurane mixed with oxygen during the imaging procedure. A loop coil (Loop Flex Coil, approximately 4 cm in diameter) was used for RF reception. Tumor progression was monitored by means of T2-weighted images obtained from 4 to 16 days after tumor implantation. The parameters for T2-weighted imaging were as follows: repetition time/echo time=3500/75 ms, matrix=125×256, field of view=25×43 mm, and section thickness=1.0 mm. The imaging plane was located across the center of the tumor injection site.

The fourth section is to proceed a brain immunofluorescence. Mice were deeply anesthetized with pentobarbital and perfused transcardially with a solution of 0.9% saline followed by 4% paraformaldehyde in PBS. Brains were dissected out and postfixed in 4% paraformaldehyde for 24 h at 4° C. They were then incubated in a 30% sucrose solution overnight at 4° C. Coronal sections were serially cut at 30 µm using a freezing microtome. Serial sections were collected in PBS containing 0.05% sodium azide, and then stored at 4° C. Immunohistochemistry was performed on floating sections. Briefly, sections were first incubated in a blocking solution for 1 h and then transferred to the rabbit antiluciferase primary antibody (1:100; Santa Cruz Biotechnology), where they remained for 18 h at 4° C. After washing, the sections were incubated with secondary DyLight488 fluorescently labeled goat-antirabbit antibody (1:1000; Rockland Immunochemicals) for 2 h at room temperature. After secondary antibody staining, the sections were counterstained with 4'-6-diamidino-2-phenylindole, mounted on glass slides using FluoreGuard mounting medium (ScyTek Laboratories), and then stored in the dark and cold until imaged. Six to eight coronal sections of each animal were analyzed using an Olympus FV1000 confocal microscope with a UPLSAPO ×20 air, ×40 air, or ×60 oil lens, and FV10-ASW1.7 software (Olympus, Shinjuku-Ku, Tokyo, Japan). A vertical scan was performed to determine the plane of greatest intensity of the fluorescent signal within the specimen; a single horizontal scan was subsequently performed at that plane. For quantification of Dox or luciferase immunoreactivity in each brain tumor region, the images were analyzed offline using Meta-Morph image analysis software (Molecular Devices).

Finally, a statistical analysis of differences between treatment conditions was performed using an unpaired Student's t-test. The Kaplan-Meier method was used to plot an animal survival curve. Significance was assessed by using the Log-Rank test. The four treatment groups (i.e., control, pulsed-HIFU exposure alone, AP-1 Lipo-Dox alone, and AP-1 Lipo-Dox followed by pulsed HIFU) were compared with respect to mean survival time, percentage increase in mean survival time, and maximal survival time. The level of statistical significance was set at $P \leq 0.05$.

Figure 5A:
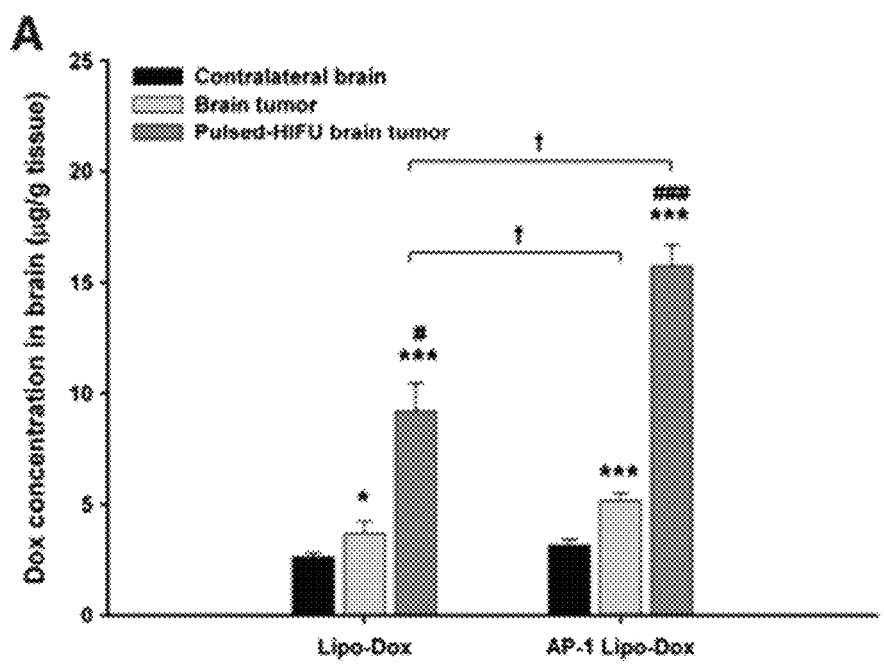
FIG. 5A is a diagram showing measurements of Lipo-Dox and AP-1 Lipo-Dox in the brain tumor and contralateral normal brain regions with or without sonication.
Figure 5B:
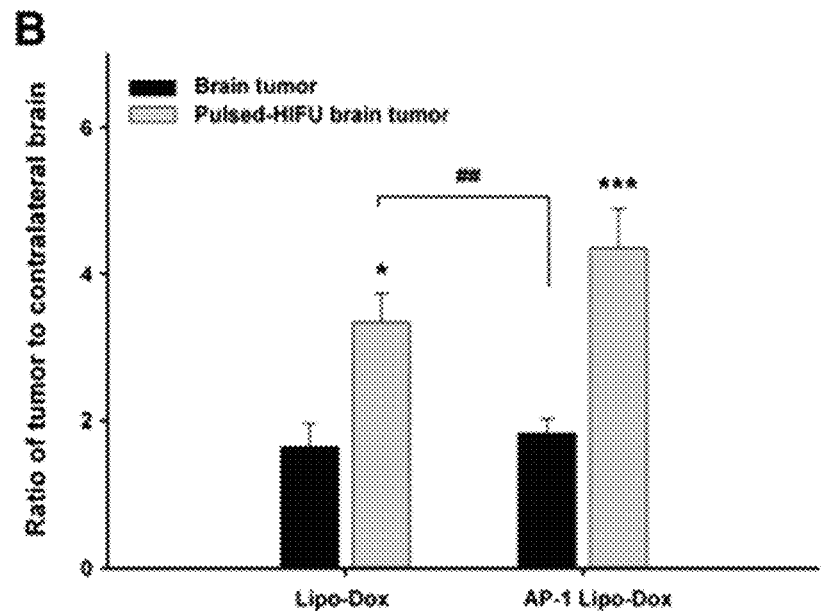
FIG. 5B is a diagram showing the derived tumor-to-contralateral brain ratios with sonication and without sonication after drug administration.

In the following, please refer to FIG. 5A and FIG. 5B. FIG. 5A is a diagram showing measurements of Lipo-Dox and AP-1 Lipo-Dox in the brain tumor and contralateral normal brain regions with or without sonication, and FIG. 5B is a diagram showing the derived tumor-to-contralateral brain ratios with sonication and without sonication after drug administration. As shown in FIG. 5A, it shows the mean concentration of Dox per unit mass for the brain tumors and the contralateral normal brain tissues with or without sonication after unconjugated Lipo-Dox or AP-1 Lipo-Dox administration. The concentration of Dox was not only significantly greater in the unsonicated tumor BBB than in the contralateral normal brain region, but it was also significantly greater at the tumor site after sonication than in the unsonicated tumor for the two forms of Lipo-Dox. Pulsed HIFU exposure administered after drug introduction increased the Dox concentration in the tumor by 147% and 202% for unconjugated Lipo-Dox and AP-1 Lipo-Dox, respectively. Furthermore, the concentration of Dox was significantly greater at the tumor site with unconjugated Lipo-Dox followed by sonication than in the unsonicated tumor treated with AP-1 Lipo-Dox without sonication. Compared to the control tumor, there were clear differences in the derived tumor-to-contralateral brain ratios in the sonicated tumors treated with either unconjugated Lipo-Dox or AP-1 Lipo-Dox. However, the derived tumor-to-contralateral brain ratio was significantly greater after sonication in the unconjugated Lipo-Dox group than in the unsonicated AP-1 Lipo-Dox group as shown in FIG. 5B.

Figure 6A:
FIGS. 6A-6E are diagrams showing immunocytochemistry of brain sections containing the glioma xenografts after administration of unconjugated Lipo-Dox without and with sonication or AP-1 Lipo-Dox without and with sonication.
Figure 6B:
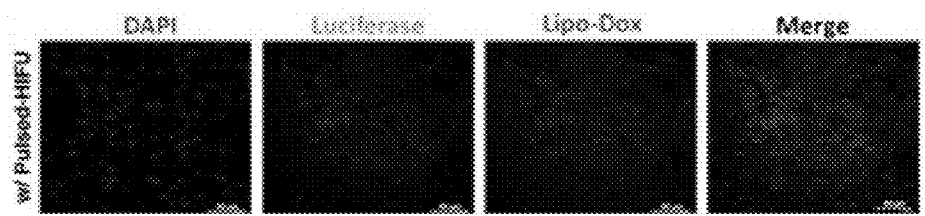
Figure 6C:
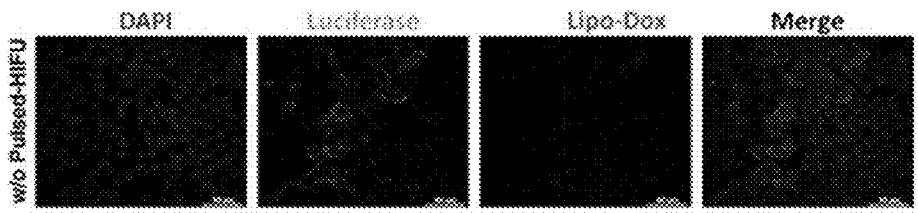
Figure 6D:
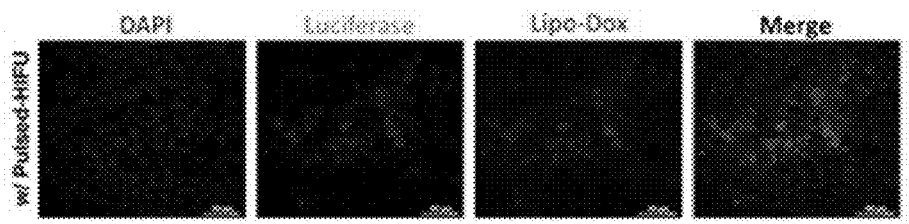
Figure 6E:
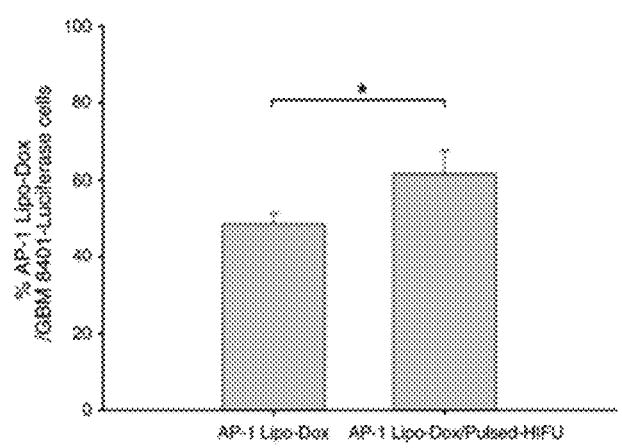

Please refer to FIGS. 6A-6E, FIGS. 6A-6E show that pulsed-HIFU exposure will result in Lipo-Dox entering the intracranial tumors in the in vivo model whether it is targeted (i.e., AP-1 Lipo-Dox) or untargeted (i.e., unconjugated Lipo-Dox). The representative images reveal that Dox (which is endogenously fluorescent) does not obviously accumulate in tumors after the administration of either form of Lipo-Dox as shown in FIG. 6A and FIG. 6C, but if sonication is added to these treatment regimes, Dox accumulation becomes evident as shown in FIG. 6B and FIG. 6D. The circulation time (3.5 h) and the amount of Dox (5 mg/kg) were the same in each group. Little-to-no colocalization of tumor cells with the luciferase gene and Dox was detected at 3.5 h after the administration of either unconjugated Lipo-Dox or AP-1 Lipo-Dox as shown in FIG. 6A and FIG. 6C. However, in both cases the Dox was markedly colocalized with tumor cells after drug injection followed by sonication as shown in FIG. 6B and FIG. 6D. The colocalized expression of tumor cells was significantly greater for treatment with AP-1 Lipo-Dox followed by sonication than for treatment with AP-1 Lipo-Dox without sonication as shown in FIG. 6E.

Figure 7:
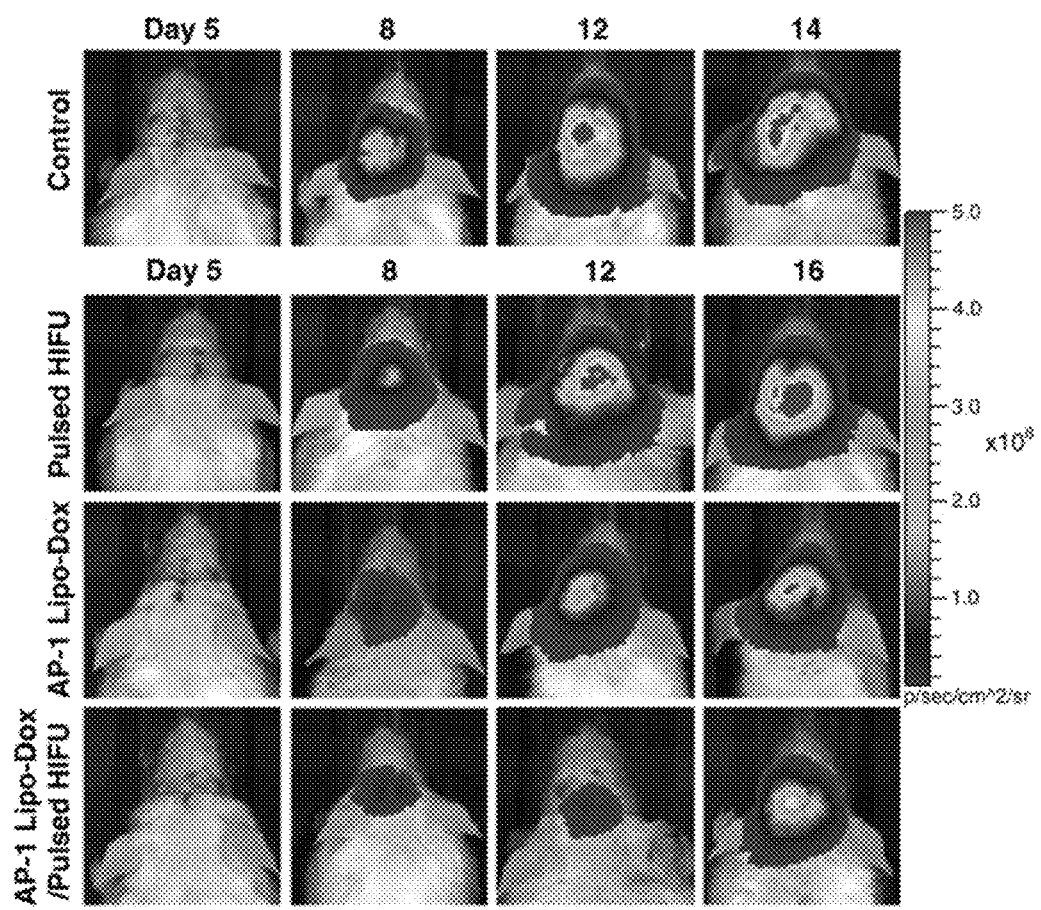
FIG. 7 is a diagram showing a biophotonic imaging of longitudinal brain tumor monitoring from days 5 to 16 after implantation.

Please refer to FIG. 7, FIG. 7 is a diagram showing a biophotonic imaging of longitudinal brain tumor monitoring from days 5 to 16 after implantation. It illustrates that treatment of an established intracranial brain tumor derived from human GBM cells with targeted Lipo-Dox (i.e., AP-1 Lipo-Dox) followed by pulsed-HIFU exposure could increase the efficacy of tumor growth inhibition relative to administering the same dose of AP-1 Lipo-Dox alone. To determine the antitumor effects, tumor-bearing mice were treated with various protocols on days 5 and 9, and tumor progressions were evaluated by IVIS imaging over time. Tumor cells spread rapidly in the untreated control mice as shown in the top panel of FIG. 7. The pattern of tumor progression in tumor bearing mice treated with pulsed HIFU alone was similar to that in the control group. Inhibition of tumor cell growth was clear with targeted AP-1 Lipo-Dox, but was even more marked for mice treated with AP-1 Lipo-Dox followed by pulsed HIFU as shown in the bottom panel of FIG. 7.

Figure 8:
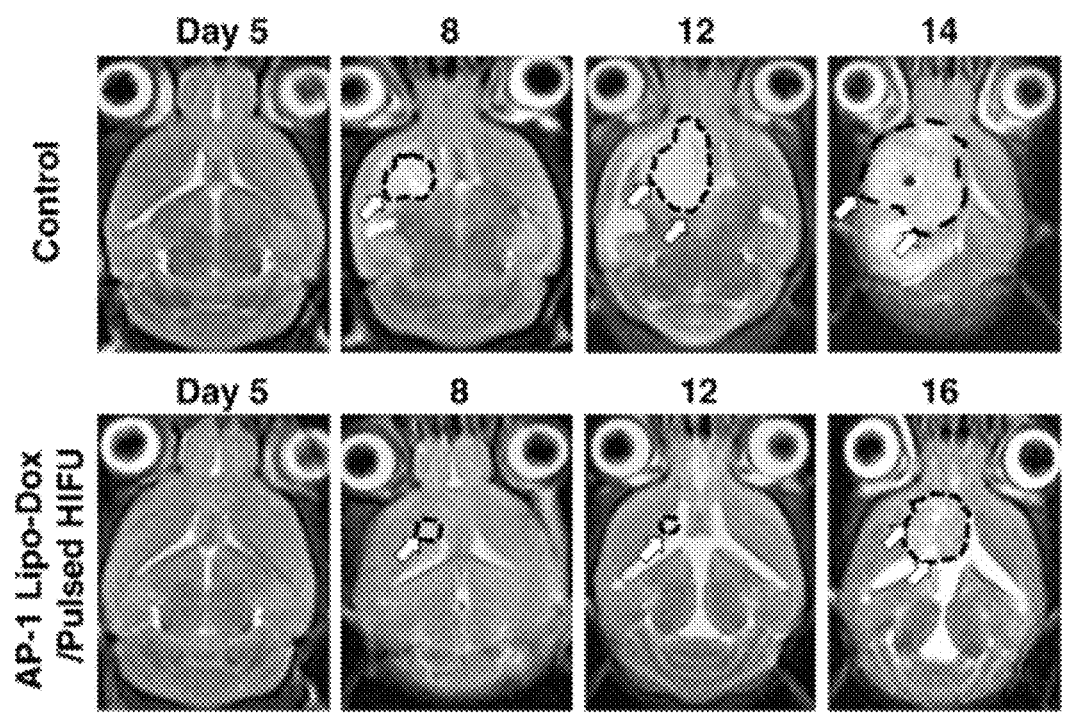
FIG. 8 is a diagram showing a representative sample of T2-weighted magnetic resonance imaging of a human GMB 8401 xenograft from days 5 to 16 post-implantation.

Please refer to FIG. 8, FIG. 8 shows tumor progression in the control and AP-1 Lip-Dox followed by pulsed HIFU was monitored by MRI. It is noted that tumor growth on days 8 and 12 after implantation was suppressed in mice treated with AP-1 Lipo-Dox followed by sonication. However, this effect was not sustained, since tumor growth in this group continued up to day 16.

Figure 9A:
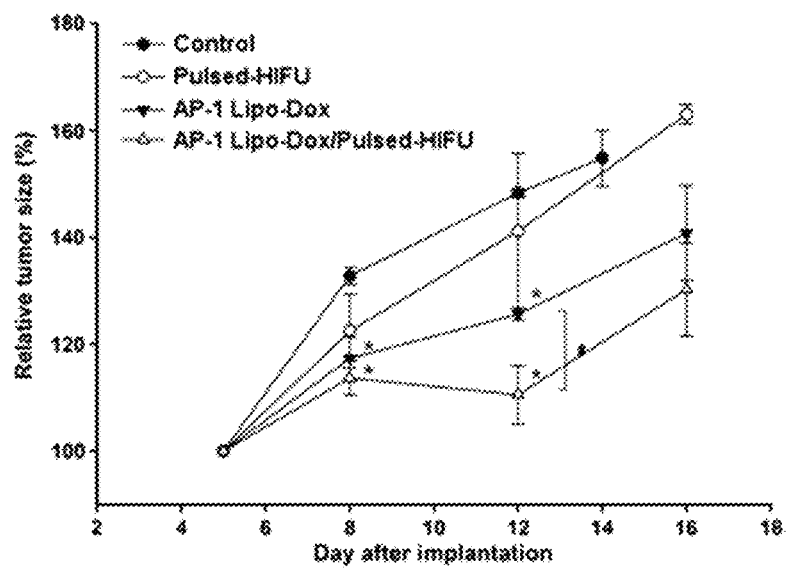
FIG. 9A is a diagram showing analysis of increases in tumor size (relative to day 5)
Figure 9B:
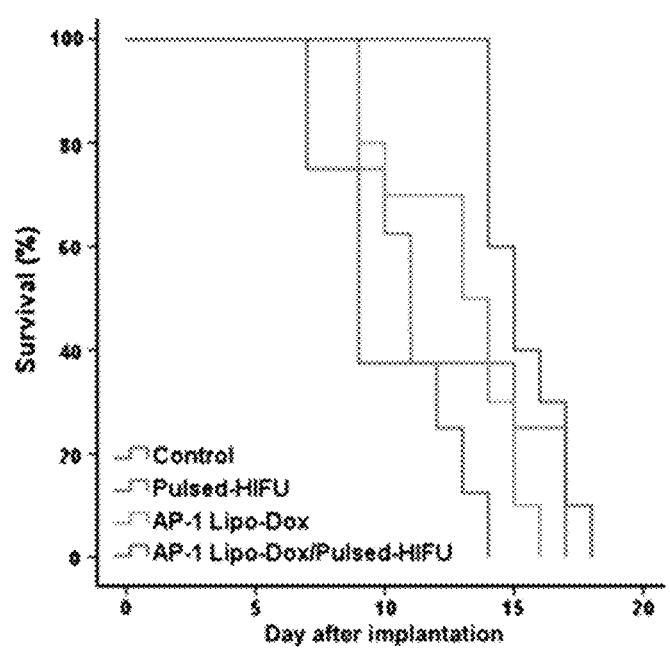
FIG. 9B is a diagram showing a Kaplan-Meier survival plot for the different treatment protocols.

Please refer to FIG. 9A and FIG. 9B, those two figures illustrate the therapeutic efficacy of the various treatment protocols on brain tumor in mice. Treatment of the tumors with AP-1 Lipo-Dox with or without sonication significantly slowed the growth of the tumor on days 8 and 12 after implantation as shown in FIG. 9A. In addition, a modest but significant improvement (P=0.017) was observed in the antitumor efficacy in mice treated with AP-1 Lipo-Dox plus sonication compared to AP-1 Lipo-Dox alone on day 12 after implantation. Sonication alone did not show any effect in limiting tumor growth. The effect of the four treatment regimes on animal survival was determined using a Kaplan-Meier survival graph as shown in FIG. 9B; the corresponding statistical data are summarized in Table 1. In the control group, the median survival was 9 days. There was a slight (22.2%) increase in median survival time ($IST_{median}$) to 11 days in mice treated with pulsed HIFU alone, but this was not statistically significant (P=0.105). The mice treated with AP-1 Lipo-Dox alone showed a significant improvement in median survival time (13 days, ISTmedian=44.4%; P=0.023 relative to the control condition). Animals treated with AP-1 Lipo-Dox followed by pulsed HIFU exhibited a promising and significant improvement, with the median survival time increased to 15 days ($IST_{median}$=66.7%; P=0.0001 relative to the control condition). These results suggest that AP-1 Lipo-Dox enhanced by pulsed HIFU at the tumor site is more effective at inhibiting tumor growth and improving animal survival than either treatment regimen alone.

TABLE 1

Efficacy of treatment protocols on brain tumor in mice

| Treatment group | Median survival (d) | $IST_{median}$ (%) | Mean survival (d)† | Maximal survival (d) | P value |
|---|---|---|---|---|---|
| Control (n = 6) | 9 | ... | 10 ± 0.9 | 14 | ... |
| Pulsed HIFU (n = 6) | 11 | 22.2 | 12.4 ± 1.2 | 17 | 0.105 |
| AP-1 Lipo-Dox (n = 10) | 13 | 44.4 | 12.8 ± 0.8 | 16 | 0.023 |
| AP-1 Lipo-Dox/ pulsed HIFU (n = 10) | 15 | 66.7 | 15.4 ± 0.5 | 18 | 0.0001‡ |

According to the abovementioned, the method and system provided in the present invention have an obvious therapeutic efficiency. Furthermore, the therapeutic efficiency of the high-dose compound as mentioned above is illustrated as the following.

Figure 10A:
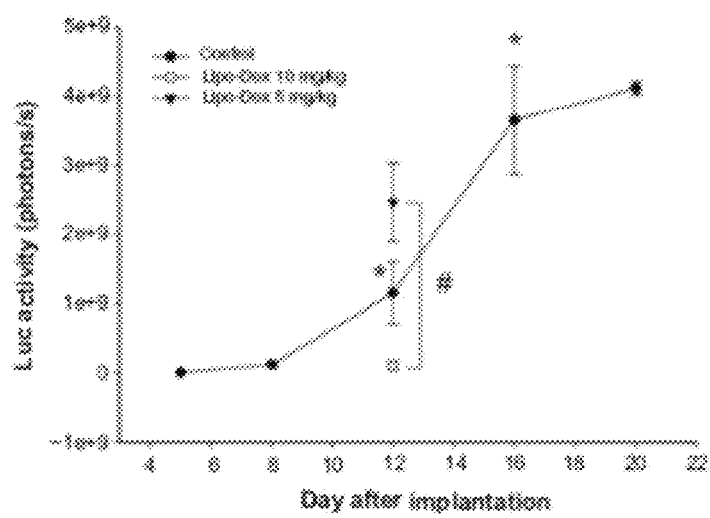
FIG. 10A is a diagram showing the growth of tumor cells in the control mice with no treatment.
Figure 10B:
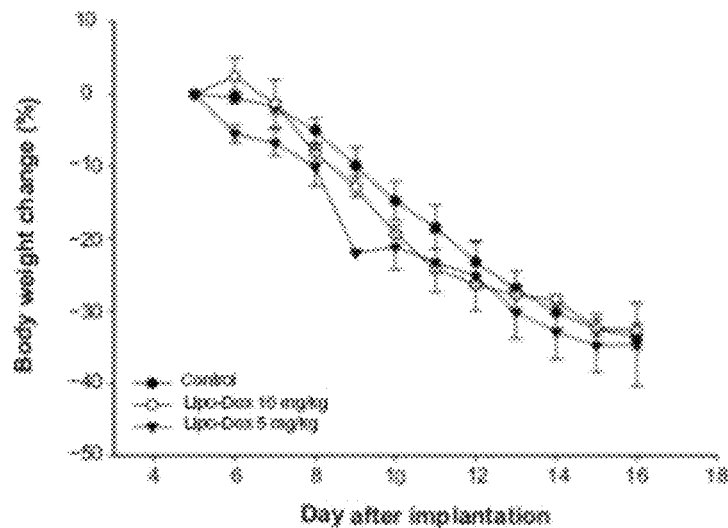
FIG. 10B is a diagram showing body weight change (relative to day 1) of tumor-bearing mice treated with different doses of liposomal doxorubicin.

Please refer to FIG. 10A and FIG. 10B. FIG. 10A shows the growth of tumor cells in the control mice with no treatment (n=3). Compared with cell numbers on day 5 after implantation, there was a significant increase in tumor cell numbers on days 12, 16, and 20. The number of tumor cells showed a significant decrease when the mice received a single dose of liposomal doxorubicin at 10 mg/kg compared with a dose of 5 mg/kg. In addition, there was no significant difference in the bodyweight change after treatment with these two doses of drug as shown in FIG. 10B.

Figure 11A:
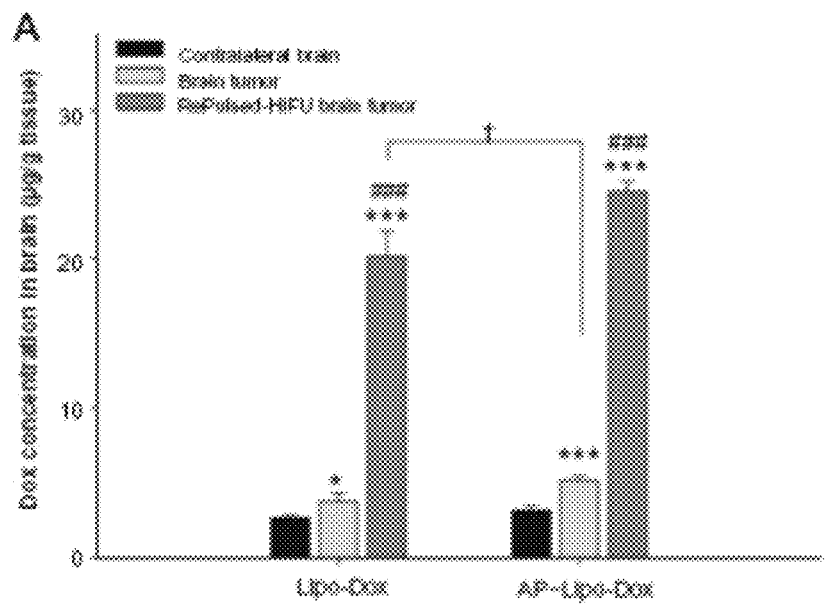
FIG. 11A is a diagram showing measurements of untargeted liposomal doxorubicin and AP-1-conjugated liposomal doxorubicin in the contralateral normal brain and the brain tumor without and with repeated sonication.
Figure 11B:
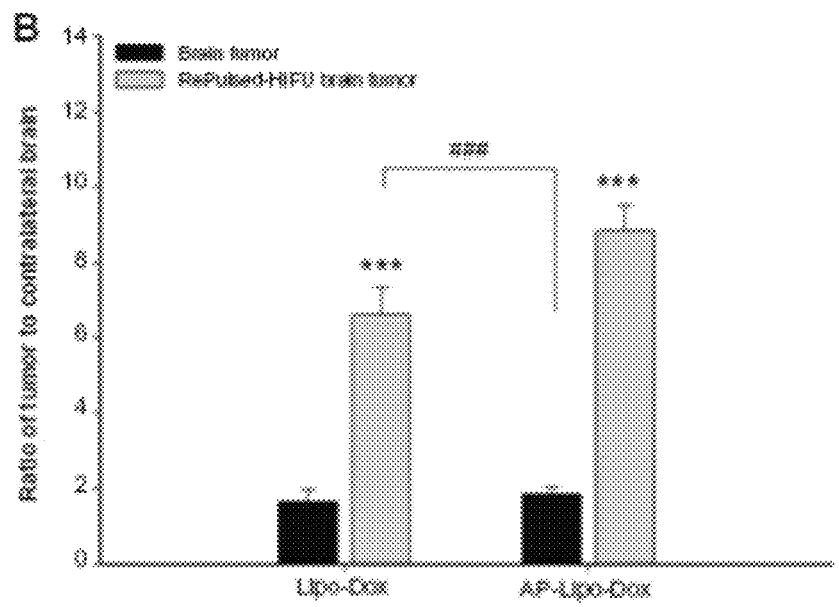
FIG. 11B is a diagram showing derived tumor-to-contralateral brain ratios without and with repeated sonication after drug administration.

Please refer to FIG. 11A and FIG. 11B. FIG. 11A shows the mean concentration of doxorubicin per unit mass for the brain tumors and the contralateral normal brain tissues with or without repeated sonication after untargeted liposomal doxorubicin or AP-1 liposomal doxorubicin administration. Not only was the concentration of doxorubicin in the nonsonicated tumor significantly greater than that in the contralateral normal brain region, but it was also found that the concentration of doxorubicin significantly increased at the tumor site after repeated sonication compared with the nonsonicated tumor for the two treatments. Repeated pulsed HIFU exposure administered after the drugs were introduced increased the doxorubicin concentration in the tumor by 441% and 374% for untargeted liposomal doxorubicin and AP-1 liposomal doxorubicin, respectively. Additionally, the concentration of doxorubicin was significantly greater at the tumor site with the untargeted liposomal doxorubicin followed by repeated sonication than for the nonsonicated tumor treated with targeted liposomal doxorubicin without sonication (P, 0.05). Compared with the control tumor, there was a significant increase in the derived tumor-to-contralateral brain ratios for the repeatedly sonicated tumor treated with either drug as shown in FIG. 11B. Importantly, however, the derived tumor-to-contralateral brain ratio was significantly greater after repeated sonication for the untargeted liposomal doxorubicin group than for the targeted liposomal doxorubicin group without sonication.

Figure 12:
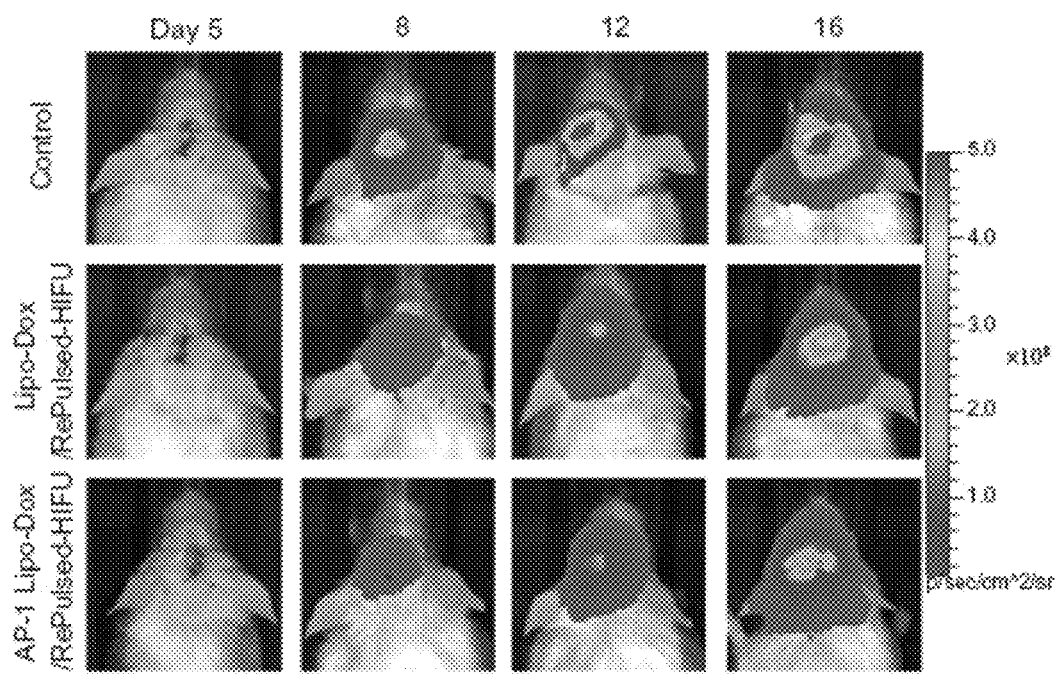
FIG. 12 is a diagram showing longitudinal bioluminescence imaging of the brain tumors was monitored from 5 to 16 days after implantation.
Figure 13A:
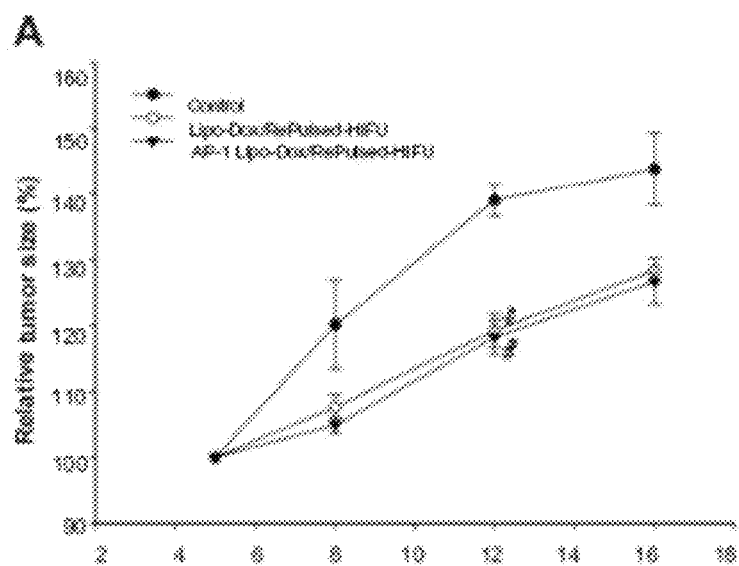
FIG. 13A is a diagram showing analysis of increases in tumor size (relative to day 5)
Figure 13B:
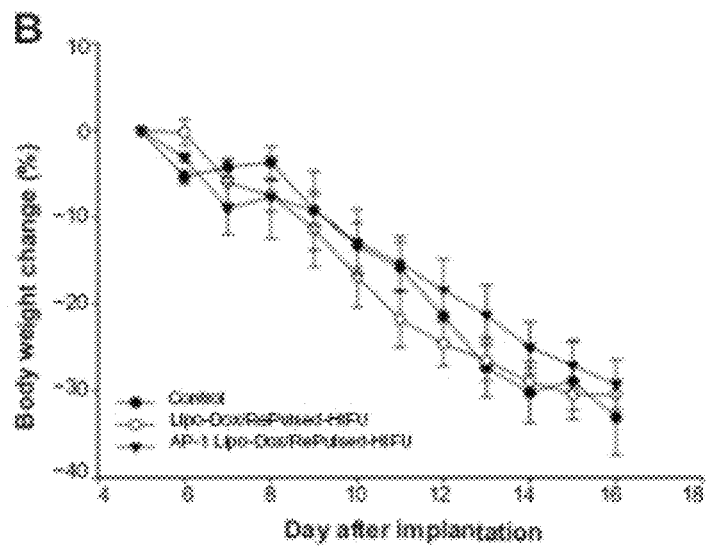
FIG. 13B is a diagram showing a bodyweight change (relative to day 5) of tumor-bearing mice treated by untargeted liposomal doxorubicin with repeated sonication and AP-1 liposomal doxorubicin with repeated sonication.

Please refer to FIG. 12 and FIGS. 13A-13B. As shown in FIG. 12, the control tumors and the effect of tumors treated on day 5 by untargeted liposomal doxorubicin or targeted liposomal doxorubicin in combination with repeated pulsed HIFU on tumor progression were monitored by bioluminescence imaging over time. Tumor cells spread rapidly in the untreated control mice as shown in the top panel of FIG. 12. When the intracranial brain tumors were treated with untargeted liposomal doxorubicin or targeted liposomal doxorubicin, in both cases followed by repeated pulsed HIFU, a similar pattern of tumor progression was followed. Tumor treatment by liposomal doxorubicin or AP-1 liposomal doxorubicin with repeated sonication significant slowed the growth of the tumors by day 12 after implantation as shown in FIG. 13A. Both treatment protocols were associated with no statistically significant decrease in body weight compared with the animals with untreated control tumors as shown in FIG. 13B.

Figure 14:
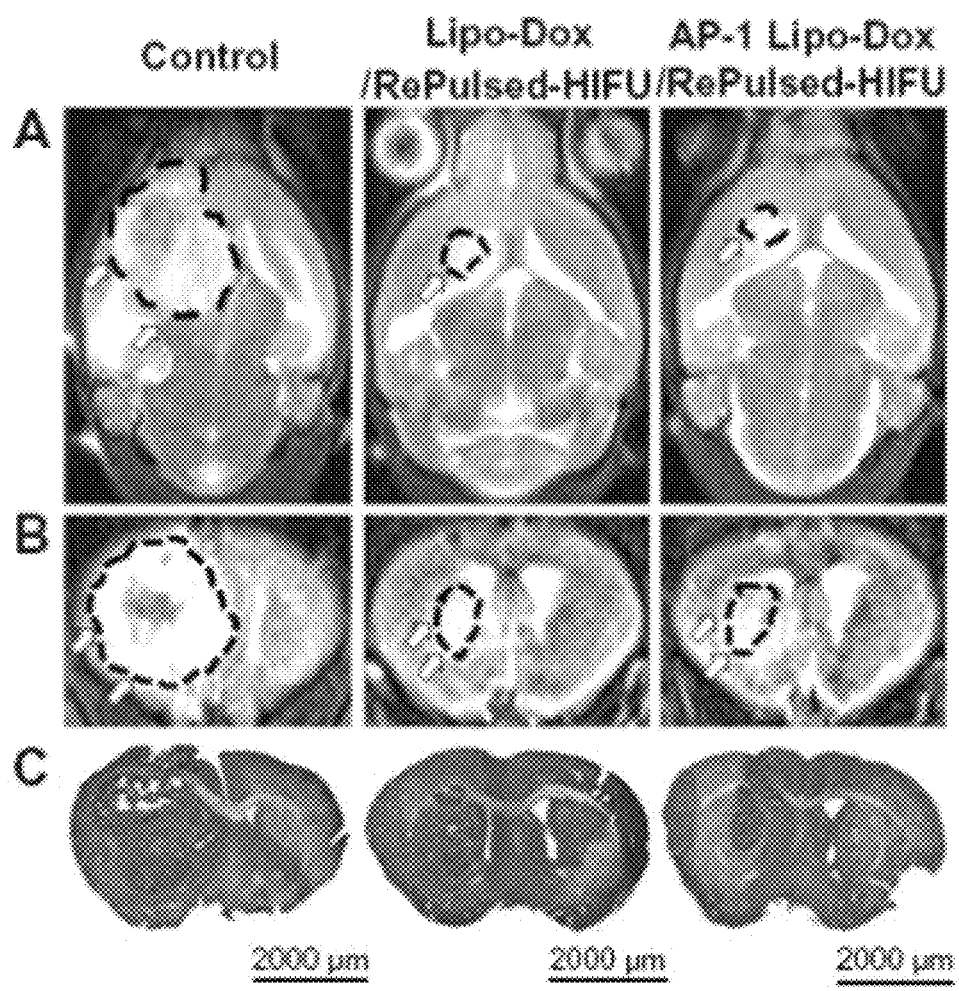
FIG. 14 is a diagram showing a MRI of mice for twelve days after tumor implantation.

Please refer to FIG. 14, it shows the effects of the various treatment protocols on tumor progression were monitored by MRI and also evaluated by hematoxylin and eosin staining on day 12 after implantation. Based on the MRI and histology, tumor progression was found to be consistent with the bioluminescence imaging (FIG. 12) and no significant difference in the tumor size was found between the treatment groups.

The applicability of repeated pulsed HIFU exposures is investigated through the abovementioned analysis when treating brain tumors with high-dose compounds. It shows that repeated sonications could significantly increase the concentration of drugs in the brain tumor. Combining the repeated sonications with either untargeted liposomal doxorubicin or targeted liposomal doxorubicin was found to have a similar and significant antitumor effect.

To sum up, the present invention provides an ultrasound-mediated drug delivery system and method for administering a compound to a targeted tissue and successfully overcomes the limitation of the prior drug delivery system. Furthermore, the clinical application of chemotherapy to brain tumors has two different types: low-dose delivery and high-dose delivery. The former type can be frequently administered for several times and has fewer side effects for specific cancers and unhealthy patients. The later type is administered with high-dose compound for one time and has an excellent efficiency on hematoma related cancers. However, the present invention has good curative effect no matter which the type is used. That is to say, by combining biology directed and physically-assisted methods, this synergistic technology can safely deliver high-dose chemotherapy specifically to a brain tumor without causing extra toxicity to the normal brain tissue or systemic side effects.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

I claim:
1. An ultrasound-mediated drug delivery method for administering an amount of AP-1 (Atherosclerotic plaque-specific Peptide-1)-conjugated liposomes to a tumor tissue at least comprising the following steps:
   providing a high-intensity focused ultrasound apparatus;
   administering the AP-1-conjugated liposomes to the tumor tissue, wherein AP-1 comprises the amino acid sequence CRKRLDRNC, and can locate the tumor tissue and bind to an IL-4 receptor of liposome;
   performing a sonication with a frequency of between about 20 kHz to 10 MHz to a blood vessel of the tumor tissue by the high-intensity focused ultrasound apparatus for a period between about 10 seconds to 30 minutes, wherein the sonication is capable of enhancing the permeability of the blood vessel to allow the administration of the AP-1-conjugated liposomes to the tumor tissue;
   if the AP-1-conjugated liposomes are administered at a dose lower than 3-5 mg/kg, then after the step of performing the sonication to the blood vessel, the step of administering the AP-1-conjugated liposomes is repeated with the lower dose to the tumor tissue, and then another sonication to the blood vessel of the tumor tissue is performed by the high-intensity focused ultrasound apparatus for the period; and
   if the AP-1-conjugated liposomes are administered at a dose higher than 10-15 mg/kg, then after the step of performing the sonication to the blood vessel, further method steps are delayed for between 1 minute and 6 hours, and then another sonication to the blood vessel of the tumor tissue is performed by the high-intensity focused ultrasound apparatus for the period.

2. The method according to claim 1 further comprising the following step:
   injecting an ultrasound contrast agent.

3. The method according to claim 2, wherein the ultrasound contrast agent comprises microbubbles.

* * * * *